United States Patent [19]

Falciani et al.

[11] 4,388,460
[45] Jun. 14, 1983

[54] CEPHALOSPORINE DESACETOXY ESTERS AND SALTS THEREOF

[75] Inventors: Marco Falciani; Renato Broggi, both of Milan, Italy

[73] Assignee: Dobfar S.p.A., Milan, Italy

[21] Appl. No.: 240,309

[22] Filed: Mar. 4, 1981

[30] Foreign Application Priority Data

Apr. 17, 1980 [IT] Italy .................. 21463 A/80

[51] Int. Cl.³ .......................................... C07D 501/22
[52] U.S. Cl. .......................................... 544/23; 544/30
[58] Field of Search ........................ 544/23, 30; 424/246

[56] References Cited

U.S. PATENT DOCUMENTS 4,107,433 8/1978 Bentley et al. .................. 544/30
4,172,198 10/1979 Kamiya et al. .................. 544/30

Primary Examiner—Paul M. Coughlan, Jr.
Attorney, Agent, or Firm—Oblon, Fisher, Spivak, McClelland & Maier

[57] ABSTRACT

Cephalosporine desacetoxy esters having the formula

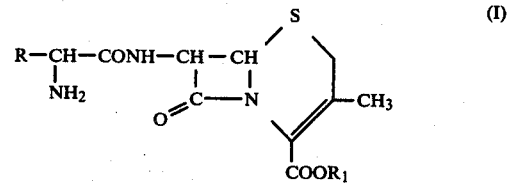

wherein R is selected from the group consisting of

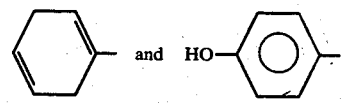

and $R_1$ is selected from the group consisting of

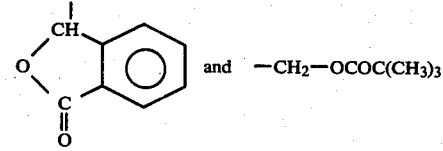

Such esters and salts thereof having antibiotic activity are prepared by reacting 7-ADCA with bromophthalide or chloromethyl pivalate in the presence of an alkylamine at a temperature in the range of 0°–70° C. The reaction product is reacted with chloride chlorohydrate of D(−)dihydrophenylglycine or D(−)p-hydroxy phenylglycine.

A salt of the compound of formula (I) is isolated from the reaction mixture, which after washing with acidic water and addition of a pharmaceutically acceptable acid is obtained by treatment with suitable solvent.

9 Claims, No Drawings

CEPHALOSPORINE DESACETOXY ESTERS AND SALTS THEREOF

The present invention relates to novel esters of desacetoxy cephalosporines, particularly cephradine and cephadroxyl, salts thereof and processes for preparing the same.

Such esters have the following structural formula

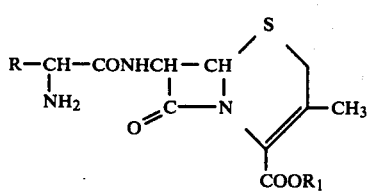

(I)

The invention also relates to the pharmaceutically acceptable salts of the esters of formula (I), and particularly chlorohydrates, p-toluene sulphonates and β-naphthalenesulphonates.

The esters of formula (I) are prepared by reacting 7-ADCA with bromophthalide or chloromethyl pivalate in the presence of an alkylamine, in a solvent selected from the group consisting of dimethylformamide, dimethyl sulphoxide, dimethylacetamide and formamide, at a temperature in the range of 0°–70° C. to provide an ester of 7-ADCA which is reacted in chlorinated aprotic polar organic solvent and in the presence of an acceptor for hydrochloric acid with chloride chlorohydrate of D(−)-dihydrophenylglycine or D(−)p-hydroxy phenylglycine, the compounds of formula (I) being isolated from the reaction mixture as salts, after washing with acidic water at pH 1.0–4.0 and addition of a pharmaceutically acceptable acid by treatment with a solvent selected from the group consisting of ethyl ether, petroleum ether and hexane.

The compounds of formula (I) and the salts thereof are antibiotics having activity similar to that of cephradine and cephadroxil.

Cephradine and cephadroxyl are compounds having the formula

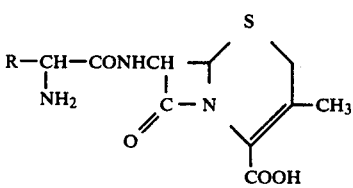

(II)

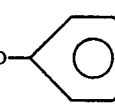

Cephradine is per se a well known product, described in U.S. Pat. No. 3,485,812.

Cephadroxyl is per se a well known product, described in U.S. Pat. No. 3,985,741.

One of the characteristics of novel esters is that once absorbed in the organism they hydrolize releasing in the time the antibiotics, from which they are derived. This release of the original antibiotics extended in time, assures the maintenance of high hematic levels over an extended period.

In order that the characteristics of the invention be more clearly understood, some unrestrictive exemplary embodiments thereof will now be described.

EXAMPLE 1

A reaction flask was charged with 2000 ml dimethylformamide, 214 g (1 mole) 7-ADCA and 213 g (1 mole) bromophthalide, the mixture was heated to 35° C. and then a dropwise addition of 101 g (1 mole) triethylamine was started, addition that was completed in 3 hours. Upon addition completion, the mixture was stirred for 2 hours at 35° C., then cooled to 0° C. and diluted with 4000 ml water, adjusting pH to 1.0 with 37% HCl and adding 3000 ml $CH_2Cl_2$. The phases were separated and the aqueous phase was extracted again with 1000 ml $CH_2Cl_2$.

The methylene phases were combined, dried over anhydrous $Na_2SO_4$ and evaporated at 40° C. to 50% volume. The methylene phase was dropwise added in 30 minutes to 4000 ml petroleum ether. A straw-coloured product was obtained, which after 1 hour under stirring was filtered, washed with petroleum ether and dried at 40° C. 190 g phthalidic ester chlorohydrate of 7-ADCA were obtained.

K.F.=0.3%.

$[\alpha]_D$ (c=1 MeOH)=+75°.

TLC=single spot.

By using dimethyl sulphoxide or dimethylacetamide as a solvent instead of DMF, analogous results were obtained. The same results were obtained by using diethylamine instead of triethylamine.

EXAMPLE 2

Phthalidic ester chlorohydrate of cephadroxyl (taldroxyl chlorohydrate)

A reaction flask was charged with 380 ml methylene chloride and 38.25 g (0.1 mole) phthalidic ester chlorohydrate of 7-ADCA. At 15° C., 10.1 g (0.1 mole) triethylamine were added to remove the hydrochloric acid of the chlorohydrate, followed by 58 g (1 mole) propylene oxide, and still at 15° C. 27.1 g (0.102 mole) D(−)p-hydroxyphenylglycine chloride chlorohydrate emidioxane solvent. The mixture was heated to 25° C. and after 1.5 hours the reaction was completed. The mixture was cooled to 0° C. and 100 ml water were added, pH was adjusted to 1.0 with conc. HCl and the phases were separated. The methylene phase was extracted again with 50 ml ice water at pH 1.0. The methylene containing the product was dried over $Na_2SO_4$, then filtered and diluted with 1500 ml petroleum ether. A white crystalline product was obtained, which after stirring for 2 hours was filtered, washed with petroleum ether and dried at 40° C.

39.8 g phthalidic ester chlorohydrate of cephadroxyl (taldroxyl chlorohydrate) were obtained.

K.F.=3.2%.

TLC=single spot (eluent formic acid/acetonitrile 1:20).

$[\alpha]_D$ (c=1, MeOH)=115° on dry base.

$E_{1\ cm}^{1\%}$ 263 nm=153.

Microbiological titre=665 mcg/mg as anhydrous cephadroxyl.

EXAMPLE 3

Phthalidic ester tosilate of cephadroxyl (taldroxyl tosilate)

A reaction flask was charged with 330 ml methylene chloride and 38.25 g (0.1 Mole) phthalidic ester chlorohydrate of 7-ADCA. At 15° C., 10.1 g (0.1 mole) triethylamine were added to remove the hydrochloric acid of the chlorohydrate, then 58 g (1 mole) propylene oxide and, still at 15° C., 27.1 g (0.102 mole) D(−)p-hydroxyphenylglycine chloride chlorohydrate emidioxane solvent. The mixture was heated to 30° C. and after 1.5 hours the reaction was completed. The mixture was cooled to 0° C. and 100 ml water were added; pH was adjusted to 1.0 with conc. HCl and the phases were separated. The methylene phase was extracted again with 50 ml ice water at pH 1.0. Separation was again carried out and the methylene phase was stratified or layered with 200 ml water, and at 0° C. 19 g (0.1 mole) p-toluensulphonic monohydrate acid were added. PH was adjusted to 1.2–1.5 and after stirring for 30 minutes, the phases were separated. The methylene solution containing phthalidic ester tosilate of cephadroxyl (taldroxyl tosilate) was dried over magnesium sulphate, filtered and diluted with 1000 ml ethyl ether.

A white crystalline product was obtained which, after 1 hour crystallization, was filtered, washed with 100 ml ethyl ether and vacuum dried at 40° C.

53.5 g phthalidic ester tosilate of cephadroxyl were obtained.

K.F.=3.1%.
TLC=single spot.
$[\alpha]_D$ (c=1, MeOH)= +92° on dry.
$E_1{}_{cm}{}^{1\%}$ at 263 nm=123.
Microbiological titre=553 mcg/mg as anhydrous cephadroxyl.

EXAMPLE 4

Phthalidic ester napsilate of cephadroxyl (taldroxyl napsilate)

A reaction flask was charged with 350 ml methylene chloride and 38.25 g (0.1 mole) phthalidic ester chlorohydrate of 7-ADCA. At 15° C., 10.1 g (0.1 mole) triethylamine were added, followed by 58 g (1 mole) propylene oxide and, still at 15° C., 27.1 g (0.102 mole) D(−)p-hydroxyphenylglicine chloride chlorohydrate. The mixture was heated to 30° C. and after 1.5 hours the reaction was completed. The solution was cooled to 0° C. and 100 ml water added; pH was adjusted to 1.0 with conc. HCl and the phases were separated. The methylene phase was washed again with 50 ml ice water, then separating again, and the methylene phase was stratified or layered with 200 ml water. At 0° C., 24.8 g (0.1 mole) β-naphthalin sodium sulphonate monohydrate were added; pH was adjusted to 1.2–1.5 with 37% HCl and after stirring for 30 minutes the phases were separated.

The methylene solution containing phthalidic ester napsilate of cephadroxyl (taldroxyl napsilate) was dried over sodium sulphate, filtered and diluted with 1100 ml ethyl ether.

A white crystalline product was obtained which, after crystallization of 20 minutes, was filtered, washed with 100 ml ethyl ether and vacuum dried at 40° C., obtaining 55 g of the above indicated product.

K.F.=2.3%.
TLC=single spot.
$[\alpha]_D$ (c=1, MeOH)= +89° on dry.
$E_1{}_{cm}{}^{1\%}$ at 263 nm=118.
Microbiological titre=510 mcg/mg as anhydrous cephadroxyl.

EXAMPLE 5

Phthalidic ester chlorohydrate of cephradine (talphradine chlorohydrate)

The same procedure with the same amounts described in Example 2 were followed, except that 21.2 g (0.102 mole) D(−)dicydrophenylglycine chloride chlorohydrate (instead of p-hydroxy phenylglycine chloride chlorohydrate) were used.

43.9 g phthalidic ester chlorohydrate of cephadine were obtained.

K.F.=2.3%.
TLC=single spot.
$[\alpha]_D$ (c=1, MeOH)= +59° on dry.
Microbiological titre=655 mcg/mg as anhydrous cephradine.

EXAMPLE 6

Phthalidic ester tosilate of cephradine (talphradine tosilate)

The same procedure with the same amounts described in Example 3 was followed, except that 21.2 g (0.102 mole) D(−)dihydrophenylglycine chloride chlorohydrate (instead of D(−)p-hydroxy phenylglycine chloride chlorohydrate) were used.

55.5 g phtalidic ester tosilate of cephradine (talphradine tosilate) were obtained.

K.F.=1.3%.
TLC=single spot.
$[\alpha]_D$(c=1, MeOH)+43° on dry.
Microbiological titre=523 mcg/mg as anyhrous cephradine.

EXAMPLE 7

Phthalidic ester napsilate of cephradine (talphradine napsilate)

The same procedure with the same amounts described in Example 4 was followed, except that 21.2 g (0.102 mole) D(−)dihydrophenylglycine chloride chlorohydrate (instead of D(−)p-hydroxy phenylglycine chloride chlorohydrate) were used.

56 g phthalidic ester napsilate of cephradine (talphradine napsilate) were obtained.

K.F.=2.6%.
TLC=single spot.
$[\alpha]_D$(c=1, MeOH)+43° on dry.
Microbiological titre=507 mcg/mg as anhydrous cephradine.

EXAMPLE 8

Pivalic ester chlorohydrate of 7-ADCA

A reaction flask was charged with 1900 ml dimethylformamide, 214 g (1 mole) 7-ADCA and 150.45 g (1 mole) chloromethyl pivalate, heating to 40° C. and adding 101 g (1 mole) triethylamine in 2 hours. The mixture was stirred at 40° C. for 6 hours. The suspension thus obtained was filtered, the residue comprising unreacted 7-ADCA and triethylamine chlorohydrate. (53 g being recovered). The filtrate was cooled to 0° C. and diluted with 3500 ml water, then pH was adjusted to 1.8 with 37% HCl, and extracting with 500 ml ethyl ether. The resulting aqueous phase was extracted with 2000 ml $CH_2Cl_2$, separated and extracted again with 800 ml CH₂Cl₂. The methylene extracts were combined, dried over Na₂SO₄ and vacuum evaporated.

An oil was obtained, which was admixed with acetone.

The crystalline product thus obtained was filtered, washed with acetone and vacuum dried at 40° C.

204 g pivalic ester chlorohydrate of 7-ADCA were obtained.

K.F.=1.2%.
$[\alpha]_D$ (c=1%, MeOH)+65°.

By using dimethyl sulphoxide or dimethylacetamide as a solvent analogous results were obtained; by using diethylamine instead of triethylamine as a base, analogous results were obtained.

EXAMPLE 9

Pivalic ester chlorohydrate of cephradine (pivphradine chlorohydrate)

A reaction flask was charged with 300 ml CH₂Cl₂ and 36.44 g (0.1 mole) pivalic ester chlorohydrate of 7-ADCA. At 20° C., 10.1 g (0.1 mole) triethylamine were added, followed by 55 g propylene oxide. The mixture was cooled to 10° C. and added with 21.5 g D(—)dihydrophenylglycine chloride chlorohydrate, the temperature was limited within +20° C. and left at said temperature for 1.5 hours. The mixture was cooled to 0° C. and added to 150 ml ice water, pH was adjusted to 1.0 with conc. HCl and the phases were separated; the methylene phase was washed again with 100 ml water at pH 1.0, then decanted and the organic phase was dried over anhydrous Na₂SO₄. The organic phase thus obtained was diluted with 1500 ml ethyl ether, obtaining a fine crystalline product of white colour which after crystallization for 1 hour was filtered, washed with 100 ml ethyl ether and vacuum dried at 40° C.

42.3 g pivalic ester chlorohydrate of cephradine were obtained.

K.F.=2.5%
TLC=single spot (eluent CH₃CN/HCOOH 20:1)
$[\alpha]_D$(c=1%, MeOH)+60° on dry.
$E_{1\,cm}^{1\%}$ at 262 nm=155.
Microbiological titre: 677 mcg/mg as anhydrous cephradine.

EXAMPLE 10

Pivalic ester tosilate of cephradine (pivphradine tosilate)

A reaction flask was charged with 330 ml CH₂Cl₂ and 36.44 g (0.1 mole) pivalic ester chlorohydrate of 7-ADCA. At 15° C., 10.1 g (0.1 mole) triethylamine (TEA) were added, followed by 58 g propylene oxide. The mixture was cooled to 10° C. and 21.5 g D(—)dihydrophenylglycine chloride chlorohydrate added and the temperature maintained at 20° C. for 1.5 hours. The mixture was cooled to 0° C. and 150 ml ice water added, pH was adjusted to 1.0 with conc. HCl and the phases were separated. The organic phase was washed again with 100 ml water at pH 1.0, then decanted, and the organic phase thus obtained was layered with 200 ml water. At 0° C., 19 g (0.1 mole) monohydrate p-toluenesulphonic acid were added; pH was adjusted to 1.2–1.5 and after stirring for 30 minutes the phases were separated. The methylene solution containing the product was dried over sodium sulphate, filtered and diluted with 1200 ml petroleum ether.

A fine white crystalline product was obtained which, after stirring for 30 minutes, was filtered, washed with 100 ml petroleum ether and vacuum dried at 40° C.

53 g pivalic ester tosilate of cephradine (pivphradine tosilate) were obtained.

K.F.=2.1%.
TLC: single spot.
$[\alpha]_D$(c=1%, MeOH)=47° on dry.
Microbiological titre=53 mcg/mg.

EXAMPLE 11

Pivalic ester napsilate of cephradine (pivphradinenapsilate)

By following the same procedure and the same amounts described in Example 10, but adding 24.8 g (0.1 mole) sodium salt of monohydrate β-naphthalenesulphonic acid, pivphradine napsilate was obtained as a crystalline solid.

Yield=52 g pivalic ester napsilate of cephradine (pivphradine napsilate.
K.F.=1.8%.
TLC=single spot.
$[\alpha]_D$(c=1%, MeOH)+45° on dry.
Microbiological titre: 529 mcg/mg as anhydrous cephradine.

EXAMPLE 12

Pivalic ester chlorohydrate of cephadroxyl (pivdroxyl chlorohydrate)

A reaction flask was charged first with 400 ml CH₂Cl₂ and then with 36.44 g (0.1 mole) pivalic ester chlorohydrate of 7-ADCA. At 10° C., 10.1 g (0.1 mole) TEA and 60 g propylene oxide were added. The mixture was cooled to 0° C. and 27.4 g (0.103 mole) D(—)dihydrophenylglycine chloride chlorohydrate emidioxane solvent added, while maintaining the temperature at 20° C. for 1.5 hours. The mixture was then cooled to 0° C. and to 200 ml ice water added, pH was adjusted to 1.0 with conc. HCl and the phases were separated. The methylene phase was washed again with 100 ml water at pH 1.0.

The organic phase thus obtained was dried over anhydrous Na₂SO₄, filtered and diluted with 1500 ml petroleum ether. A crystalline white product was obtained which after stirring for 30 minutes was filtered, washed with 200 ml petroleum ether and vacuum dried at 40° C.

41 g pivalic ester chlorohydrate of cephadroxyl (pivdroxyl chlorohydrate were obtained.
K.F.=2.1%.
TLC=single spot. Eluent CH₃CN/HCOOH 20:1.
$[\alpha]_D$(c=1%, MeOH)= +120° on dry.
Microbiological titre=700 mcg/mg as anhydrous cephadroxyl.

EXAMPLE 13

Pivalic ester tosilate of cephadroxyl (pivdroxyl tosilate)

The same procedure with the same amounts described in Example 12 was followed. The methylene phase was layered with 200 ml water, then added with 19 g (0.1 mole) monohydrate p-toluenesulphonic acid, pH was adjusted to 1.2 and after 30 minutes the phases were separated. The methylene layer was dried on magnesium sulphate, filtered and the filtrate was dropwise added in 30 minutes to 1300 ml petroleum ether under stirring. The crystalline product thus formed was filtered, washed with 200 ml petroleum ether and vacuum dried at 40° C.

55 g pivalic ester tosilate of cephadroxyl (pivdroxyl tosilate) were obtained.

K.F.=1.8%.
TLC=single spot
$[\alpha]_D(c=1\%, MeOH)= +93°$ on dry.
Microbiological titre=550 mcg/mg as anhydrous cephadroxyl.

EXAMPLE 14

Pivalic ester napsilate of cephadroxyl (pivdroxyl napsilate)

The same procedure with the same amounts described in Example 12 was followed. The methylene layer obtained after washings with water was layered with 250 ml water and added with 24.8 g (0.1 mole) sodium salt of monohydrate β-naphthalenesulphonic acid, pH was adjusted to 1.2–1.3 and after 30 minutes the phases were separated.

The methylene obtained was dried over sodium sulphate, filtered and dropwise added in 30 minutes to 1500 ml petroleum ether. The crystalline product thus formed was filtered, washed with 200 ml petroleum ether and vacuum dried at 40° C.

56.6 g pivalic ester napsilate of cephadroxyl (pivdroxyl napsilate) were obtained.

K.F.=2.3%.
TLC=single spot.
$[\alpha]_D(c=1\%, MeOH)= +90°$ on dry.
$E_{1\ cm}^{1\%}$ at 262 nm=120.
Microbiological titre=539 mcg/mg as anhydrous cephadroxyl.

In all of the above described examples, the use of acceptors for HCl other than propylene oxide, such as sodium bicarbonate and acetamide, would lead to analogous results.

What we claim is:

1. Esters of desacetoxy cephalosporines having the formula $$R-CH-CONHCH-CH \begin{matrix} S \\ \\ \end{matrix} \begin{matrix} \\ CH_3 \\ COOR_1 \end{matrix}$$ (I)

wherein R is selected from the group consisting of:

[cyclohexadienyl] and HO—[phenyl]— and $R_1$ is selected from the group consisting of

[structure with CH, O, C=O attached to benzene ring]

and —CH₂—OCOC(CH₃)₃.

2. Pharmaceutically acceptable salts of the esters of claim 1.

3. Pharmaceutically acceptable salts of the esters of claim 1, selected from the group consisting of chlorohydrates, p-toluenesulphonates and β-naphthalenesulphonates of such esters.

4. The desacetoxy cephalosporine esters of claim 1 wherein R is the 1,4-cyclohexadienyl radical.

5. The desacetoxy cephalosporine ester of claim 4 wherein $R_1$ is —CH₂—OCOC(CH₃)₃.

6. The desacetoxy cephalosporine esters of claim 1 wherein R is the p-hydroxyphenyl radical.

7. The desacetoxy cephalosporine ester of claim 6 wherein $R_1$ is —CH₂—OCOC(CH₃)₃.

8. The desacetoxy cephalosporine ester of claim 6 wherein $R_1$ is

[structure with CH, O, C=O attached to benzene ring]

9. The desacetoxy cephalosporine ester of claim 4 wherein $R_1$ is

[structure with CH, O, C=O attached to benzene ring]

* * * * *